United States Patent [19]
Kaiho et al.

[11] Patent Number: 4,782,154
[45] Date of Patent: Nov. 1, 1988

[54] ISOQUINOLINE DERIVATIVES

[75] Inventors: Tatsuo Kaiho; Seitaro Kajiya; Kengo Otsuka, all of Kanagawa; Masahiko Maruyama; Makoto Hirayama, both of Chiba, all of Japan

[73] Assignee: Mitsui Toatsu Chemicals, Inc., Tokyo, Japan

[21] Appl. No.: 75,828

[22] Filed: Jul. 17, 1987

[30] Foreign Application Priority Data

Aug. 27, 1986 [JP] Japan ................................ 61-198977

[51] Int. Cl.$^4$ ........................................... C07D 217/16
[52] U.S. Cl. ................................................... 546/141
[58] Field of Search ........................................ 546/141

[56] References Cited

U.S. PATENT DOCUMENTS 4,639,521  1/1987  Sannohe et al. .................... 546/141

FOREIGN PATENT DOCUMENTS 61-291570  12/1986  Japan ................................ 546/141
61-291569  12/1986  Japan .
62-19570   1/1987   Japan ................................ 546/141
2162178A   1/1986   United Kingdom ................ 546/141

Primary Examiner—Richard L. Raymond
Assistant Examiner—James H. Turnipseed
Attorney, Agent, or Firm—Browdy and Neimark

[57] ABSTRACT

The isoquinoline derivatives represented by the following general formula (I) are useful as cardiotonics having high cardiotonic activity and low toxicity:

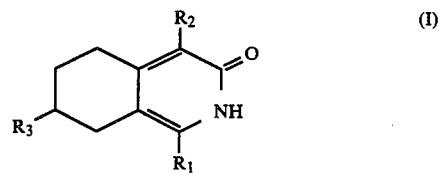

where $R_1$ represents a lower $C_1$–$C_4$ alkyl group or cyclopropyl group, $R_2$ represents formyl group, lower $C_1$–$C_4$ alkanoyl group and benzoyl group, lower $C_1$–$C_4$ alkyl group, lower $C_1$–$C_4$ alkenyl group, lower $C_1$–$C_4$ hydroxy substituted alkyl group, $C_1$–$C_4$ perfluoroalkyl group and $R_3$ represents 4-pyridyl group or 2-pyridyl group respectively, and the therapeutically acceptable salts thereof are also useful as cardiotonics.

5 Claims, No Drawings

ISOQUINOLINE DERIVATIVES

BACKGROUND OF THE INVENTION

1. Field of the Invention

This invention concerns novel isoquinoline derivatives and therapeutically acceptable addition salts thereof useful as cardiotonics.

2. Description of the Prior Art

Digitalis pharmaceuticals such as digoxin or digitoxin have been used as cardiotonics for the therapy of heart failure.

Cardiotonic activity has also been reported for nicotinonitrile derivatives (for instance, referred to Japanese patent laid-open No. Sho 57-70868), imidazolone derivatives (for instance, referred to Japanese patent laid-open No. Sho 59-155368) and dihydropyridadine derivatives (for instance, referred to Japanese patent laid-open No. Sho 58-74679).

As an isoquinoline derivative having cardiotonic activity, a compound represented by the general formula (I) described in the present specification, wherein $R_1$ represents methyl group and $R_2$ represents cyano or acetyl group has already been filed as Japanese patent application No. Sho 61-623.

Digitalis pharmaceuticals used at present for therapy require highly skilled techniques for use since their safety range is narrow and they provide a problem of causing undesirable side activity such as irregular pulses.

Further, nicotinonitrile derivatives, imidazolone derivatives, dihydropyridadinone derivatives, etc., which have already been reported also involve problems such as low cardiotonic activity, narrow safety range, increase in the number of myocardiac movement or high animal toxicity.

The present inventors have continued an earnest study with an aim of obtaining a compound having a broad safety range and with no side activity and, as a result, have accomplished this invention based on the findings that isoquinoline derivatives have high cardiotonic activity and less toxicity.

SUMMARY OF THE INVENTION

The foregoing object of this invention can be attained in accordance with this invention by isoquinoline derivatives represented by the general formula (I):

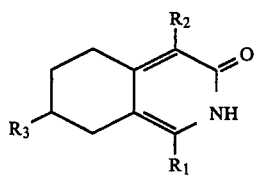

(I)

(where $R_1$ represents a lower $C_1$–$C_4$ alkyl group or cyclopropyl group, $R_2$ represents formyl group, lower $C_1$–$C_4$ alkanoyl group, benzoyl group, lower $C_1$–$C_4$ alkyl group, lower $C_1$–$C_4$ alkenyl group, $C_1$–$C_4$ hydroxy substituted alkyl group and $C_1$–$C_4$ perfluoroalkyl group and $R_3$ represents 4-pyridyl or 2-pyridyl group), as well as therapeutically accetable salts thereof.

The compound represented by the formula (I) according to this invention can also be in a tautomertic isomer represented by the formula (II):

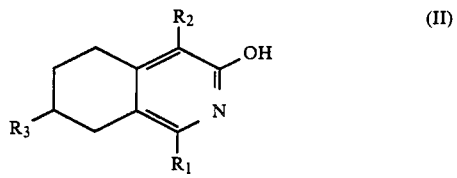

(II)

and the compound (II) is of course included within this invention.

The isoquinoline derivatives according to this invention can be produced, for example, by the following procedures.

That is, as shown by the reaction route A, 4- (also 2-) pyridylcyclohexanone, i.e., the compound (VIII) can be synthesized by the method of Japanese patent application No. Sho 61-86060, that is, Diels-Alder reaction of chloroprene and vinyl pyridine, followed by hydrolysis.

Reaction route A

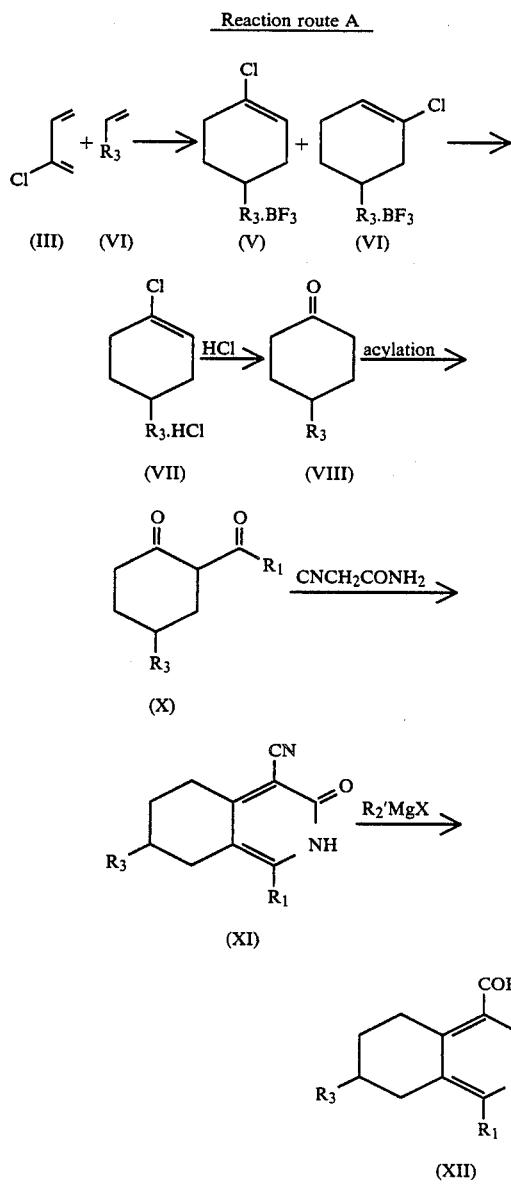

The compound (VIII) can also be synthesized by the methods of Japanese patent application No. Sho 60-131940, Japanese patent application No. Sho 60-144008 and the like.

The compound (X) can be produced by conducting acylation for the compound (VIII) using an appropriate acylating agent, that is, alkanoyl imidazole, acid anhydride, carboxylic chloride or fatty acid ester in the presence of sodium alkoxide, sodium hydride, boron trifluoride, acetic acid, lithium diisopropyl amide or zinc chloride.

Further, the compound (X) can also be produced by converting the compound (VIII) into an enamine by cyclic amine such as pyrrolidine and morpholine and then acylating with acid anhydride or carboxylic chloride.

Then, compound (XI) can be produced by condensating the compound (X) with cyanoacetoamide in the presence, for example, of a secondary amine such as piperidine or diethylamine, or in the presence of sodium alkoxide in alcohol such as methanol and ethanol.

Compound (XII) can be produced by subjecting the compound (XI) to Grignard reaction.

Further, the compound (XII) can also be produced through the reaction route B by reacting the compound (X) and alkanoylacetoamide in the presence of a basic catalyst such as piperidine, diethylamine or potassium carbonate in an alcohol such as methanol or ethanol or water.

Reaction route B

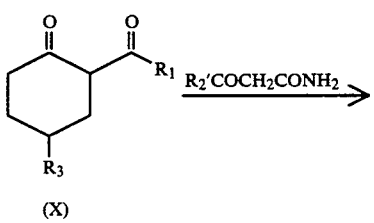

(X)

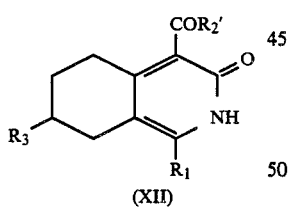

(XII)

By subjecting the compound (XII) through the reaction route C to Wolff-Kishner reduction, the compound (I) where the 4-position $R_2$ is an alkyl group can be obtained.

Reaction Route C

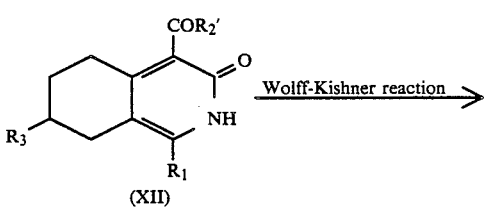

(XII)

Reaction Route C

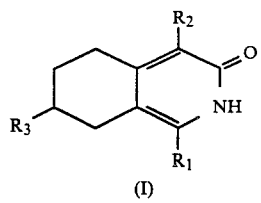

(I)

Compound (XIV) can be obtained through the reaction route D by hydrolyzing the compound (XI) into the compound (XIII) and formylating the 4-position thereof with chloroform and potassium hydroxide, for example, in ethanol-water through the Reimer-Tiemann reaction.

Compound (XV) in which the 4-position is methyl group can be produced by subjecting the compound (XIV) to Wolff-Kishner reduction.

Reaction route D

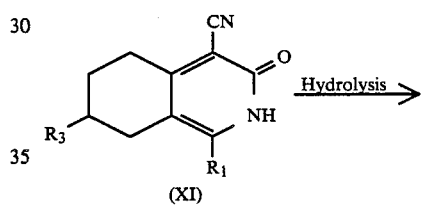

(XI)

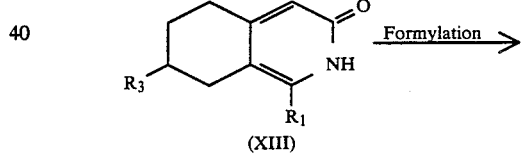

(XIII)

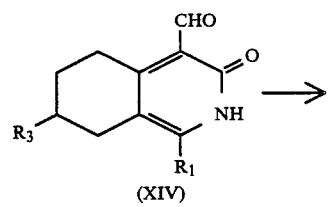

(XIV)

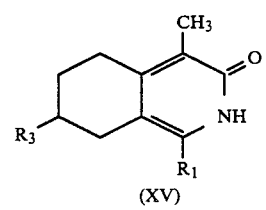

(XV)

Compound (XVI) can be obtained through the reaction route E by perfluoroalkylating the compound (XIII) using the reagent of Umemoto, et al (Chem. Lett., 1981, 1663).

Reaction route E

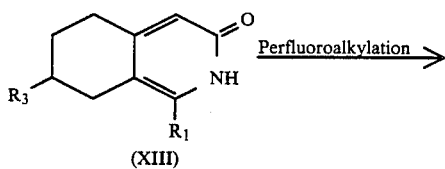

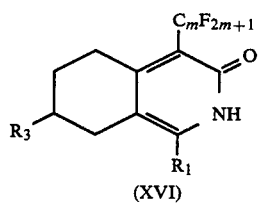

Compound (XVII) can be obtained through the reaction route F by reducing the compound (XII) with a reducing agent, for example, sodium borohydride.

Reaction route F

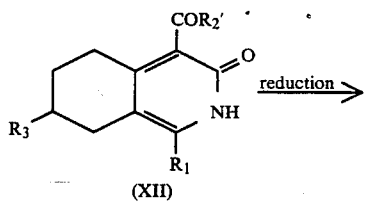

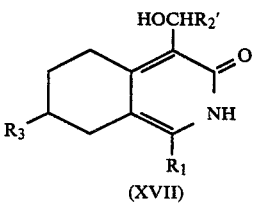

Compound (XVIII) can be obtained by conducting the Grignard reaction on the compound (XII) in ether or tetrahydrofuran as shown by the reaction route G.

Further, compound (XIX) can be obtained by dehydrating the compound (XVIII) by using a strong acid such as trifluoroacetic acid or the like.

Reaction route G

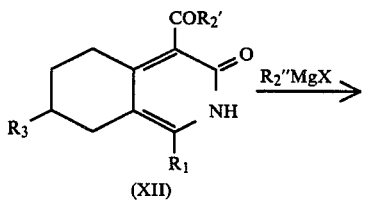

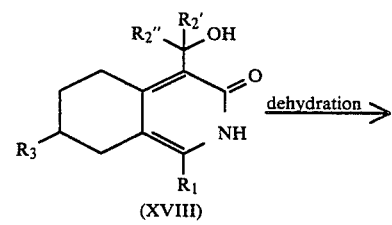

-continued
Reaction route G

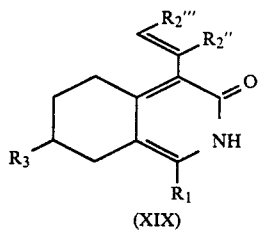

In each of the reaction routes, $R_1$ represents a lower $C_1$–$C_4$ alkyl group or cyclopropyl group, $R_2$ represents formyl group, lower $C_1$–$C_4$ alkanoyl group, benzoyl group, lower $C_1$–$C_4$ alkyl group, lower $C_1$–$C_4$ alkenyl group, $C_1$–$C_4$ hydroxy substituted alkyl group and $C_1$–$C_4$ perfluoroalkyl group, $R_3$ represents 4-pyridyl or 2-pyridyl group, $R'_2$, $R''_2$, $R'''_2$ represent hydrogen or lower $C_1$–$C_3$ alkyl and $C_mF_{2m+1}$ represents perfluroalkyl group.

In the case of using a compound according to this invention as a cardiotonic agent it may be administrated, desirably, orally but is may be administrated not orally such as intravenously and the compound may be formulated in various kinds of forms suitable to the respective methods.

For instance, the compounds and the salts thereof according to this invention can be formulated by themselves or in admixture with non-toxic pharmaceutically allowable auxiliary agents such as shaping agents, carriers, binders, stabilizers, diluents and flavors.

In the case of orally administering chemicals, they may be formulated into tablets, capsules, granules, powders, syrups or elixirs and in the case of administering them not orally, they can be formulated into injection solutions, etc.

The dosage to human beings is determined by physicians considering the state and the age of the patient, method of administration or the like. In the oral administration, for example, a dosage of about 0.01 mg–10 mg per 1 kg body weight per one day is selected with no particular restriction thereto.

According to this invention, novel isoquinoline derivatives can be produced, which are useful as cardiotonics and which are compounds with low toxicity and broad safety range.

The usefulness of the compound as the cardiotonics have been confirmed by their effectiveness in the standard pharmacological test methods.

For instance, the usefulness of the compounds has been demonstrated in that they exhibit noticeable recovery of the function of heart under anesthetization reduced by the intravenous administration of propranolol.

EXAMPLE 1

4-acetyl-1-ethyl-7-(4-pyridyl)-5,6,7,8-tetrahydro-3(2H)isoquinolinone 1-(1)2-propionyl-4-(4-pyridyl)cyclohexanone 4-(4-pyridyl)cyclohexanone (3 g) was dissolved in toluene (20 g) and, after adding pyrrolidine (3.2 g), they were heated under reflux for three hours to conduct azeotropic dehydration while attaching water descending pipe.

After cooling, they were concentrated and dioxane (22 g) and propionic acid anhydride (9.7 g) were added to residue and stirred under heating at 40° C. for 13.5 hours.

Water (15 ml) was added to the reaction solution and heated under reflux for one hour, followed by cooling.

After adding chloroform (16 ml), the solution is rendered alkaline with an aqueous 2N-sodium hydroxide solution to remove chloroform layer and, further, the aqueous layer was washed with chloroform (10 ml).

Successively, after adding ammonium chloride (27 g) to the aqueous layer, they were extracted with chloroform (20 ml×3) dried with sodium sulfate and concentrated to obtain 3.1 g of a crude product of 2-propionyl-4-(4-pyridyl)cyclohexanone.

1-(2)  4-cyano-1-ethyl-7-(4-pyridyl)-5,6,7,8-tetrahydro-3(2H)isoquinolinone 2-propionyl-4-(4-pyridyl)cyclohexanone (3.1 g) obtained as described above was dissolved in ethanol (35 ml) and, after adding cyanoacetoamide (1.26 g) and 28% sodium methylate/methanol solution (0.58 g), they were heated under reflux for 6 hours.

After cooling, 0.5N-hydrochloric acid (5 ml) was added for neutralization and, after stirring at 5° C. for 2 hours, acetone (30 ml) was added and left for one night.

The precipitate was collected by filtration, dissolved in a mixed solvent (20 ml) of ethanol/chloroform (1:1) and purified on silica gel column chromatography to obtain 4-cyano-1-ethyl-7-(4-pyridyl)-5,6,7,8-tetrahydro-3(2H)isoquinolinone (1 g).

1-(3)  4-acetyl-1-ethyl-7-(4-pyridyl)-5,6,7,8-tetrahydro-3(2H)isoquinolinone 4-cyano-1-ethyl-7-(4-pyridyl)-5,6,7,8-tetrahydro-3(2H)isoquinolinone (1 g) was added gradually under a nitrogen gas stream to 20% methylmagnesium bromide/tetrahydrofuran (10 ml). After the addition, they were heated under reflux for 3 hours.

After cooling, the reaction solution was poured into 6N-hydrochloric acid (10 ml) and then tetrahydrofuran was removed by distillation. 6N-hydrochloric acid (10 ml) was further added and heated at 80° C. for 3 hours.

After cooling, they were washed with chloroform (10 ml×2) and the aqueous layer was adjusted to pH 9 with 10N-sodium hydroxide and extracted with chloroform (20 ml×2).

The chloroform extract was washed with 0.08N-sodium hydroxide (5 ml) for three times and, after water washing, discolored and purified on silica gel column chromatography.

After concentrating the liquid effluent, it was recrystallized with ethanol to obtain 4-acetyl-1-ethyl-7-(4-pyridyl)-5,6,7,8-tetrahydro-3(2H)isoquinolinone (0.62 g).

mp 285°~295° C. (decomposition)

IR $\nu_{max}^{KBr}$ cm$^{-1}$: 1680, 1630, 1530, 1470, 1410, 1350, 1200, 1170, 1080

NMR(DMSO-D6) δ ppm: 1.12(t, J=8 Hz, 3H), 1.6~2.2(m, 3H), 2.44(s, 3H), 2.4~3.2(m, 6H), 7.38(m, 2H), 8.54(m, 2H), 11.9(br s, 1H)

| Elementary analysis C$_{18}$H$_{20}$N$_2$O$_2$ | | | |
|---|---|---|---|
| | C | H | N |
| Calcd. value (%) | 72.95 | 6.80 | 9.45 |
| Measured value (%) | 72.90 | 6.75 | 9.36 |

EXAMPLE 2

4-acetyl-1-butyl-7-(4-pyridyl)-5,6,7,8-tetrahydro-3-(2H)isoquinolinone

The compound was synthetized in the same manner as in Example 1 excepting for using valeric acid anhydride instead of propionic acid anhydride.

2-(1)  1-butyl-4-cyano-7-(4-pyridyl)-5,6,7,8-tetrahydro-3(2H)isoquinolinone

NMR(DMSO-D6) δ ppm: 0.90(t, J=8 Hz, 3H), 1.1~1.7(m, 4H), 1.7~2.2(m, 2H), 2.3~2.7(m, 3H), 2.7~3.1(m, 4H), 7.26(m, 2H), 8.40(m, 2H), 12.2(br s, 1H)

2-(2)  4-acetyl-1-butyl-7-(4-pyridyl)-5,6,7,8-tetrahydro-3-(2H)isoquinolinone mp 223°~224° C.

IR $\nu_{max}^{KBr}$ cm$^{-1}$: 1680, 1630, 1600, 1520, 1470, 1420, 1350, 1210, 1170

NMR(CDCl$_3$) δ ppm: 0.96(t, J=8 Hz, 3H), 1.2~2.3(m, 8H), 2.62(s, 3H), 2.3~3.1(m, 5H), 7.18(d, J=6 Hz, 2H), 8.52(d, J=6 Hz, 2H), 13.5(br s, 1H)

EXAMPLE 3

4-acetyl-1-cyclopropylcarbonyl-7-(4-pyridyl)-5,6,7,8-tertrahydro-3(2H)isoquinolinone 3-(1)  2-cyclopropylcarbonyl-4-(4-pyridyl)cyclohexanone 4-(4-pyridyl)cyclohexanone (5.3 g) was dissolved in toluene (40 ml) and, after adding pyrrolidine (5.6 g), they were heated under reflux for 3 hours for azeotropic dehydrogen while attaching water descending pipe.

After cooling, they were concentrated and the residue was dissolved in benzene (40 ml) and, after cooling to 10° C., a solution of cyclopropionic acid chloride (3.9 g) in benzene (10 ml) was dropped.

After the dropping, they were heated under reflux for 8 hours, and after cooling, the benzene layer was separated with the addition of water (20 ml).

After concentration, the residue was purified on silica gel column chromatography to obtain a crude product (7.5 g) of 2-cyclopropylcarbonyl-4-(4-pyridyl)cyclohexanone.

3-(2)  4-cyano-1-cyclopropylcarbonyl-7-(4-pyridyl)-5,6,7,8-tetrahydro-3(2H)isoquinolinone Crude product of 2-cyclopropylcarbonyl-4-(4-pyridyl)cyclohexanone (7.5 g) was dissolved in ethanol (100 ml) and, after adding cyanoacetoamide (2.6 g) and piperidine (0.5 ml), heated under reflux for 5 hours.

After cooling, they were concentrated, chloroform (20 ml) was added to the residue and, after filtering off the precipitates, the filterate was purified on silica gel column chromatography to obtain 4-cyano-1-cyclopropylcarbonyl-7-(4-pyridyl)-5,6,7,8-tetrahydro-3(2H)isoquinolinone (0.44 g).

mp. 285°~295° C. (decomposition)

NMR(DMSO-D6+CF$_3$COOH) δ ppm: 0.9~1.2(m, 4H), 1.8~2.3(m, 4H), 2.4~3.4(m, 4H), 7.9(m, 2H), 8.8(m, 2H)

3-(3)  4-acetyl-1-cyclopropylcarbonyl-7-(4-pyridyl)-5,6,7,8-tetrahydro-3(2H)isoquinolinone The compound obtained in the same manner as in Example 1-(3).

mp 273°~275° C.

IR $\nu_{max}^{KBr}$ cm$^{-1}$: 1690, 1620, 1610, 1540, 1470, 1420, 1360, 1210, 1200, 1170

NMR(CDCl₃) δ ppm: 0.9~1.3(m, 4H), 1.6~2.3(m, 4H), 2.60(s, 3H), 2.4~3.2(m, 5H), 7.14(m, 2H), 8.46(m, 2H), 12.0(br s, 1H)

EXAMPLE 4

1-methyl-4-propionyl-7-(4-pyridyl)-5,6,7,8-tetrahydro-3(2H)isoquinolinone

Magnesium flakes (1.8 g) were added to ether (40 ml) and ethyl bromide (8.2 g) was slowly dropped under a nitrogen gas stream. After magnesium was dissolved, 4-cyano-1-methyl-5,6,7,8-tetrahydro-3(2H)isoquinolinone (4 g) was added. Subsequently, after dropping tetrahydrofuran (15 ml), they were heated to remove ether by distillation. Tetrahydrofuran (50 ml) was further added and heated under reflux for 5 hours.

The reaction solution was poured into 6N-hydrochloric acid and then heated again under reflux for 30 minutes.

After cooling, the organic solvent was removed through distillation under a reduced pressure and, after adjusting pH to 8.5 with an aqueous 10N-solution sodium hydroxide, extracted with chloroform (200 ml×2).

The extract was dried, concentrated and recrystallized from ethanol to obtain 1-methyl-4-propionyl-7-(4-pyridyl)-5,6,7,8-tetrahydro-3(2H)isoquinolinone (1.2 g).

mp 295° C. (decomposition)

IR $\nu_{max}^{KBr}$cm⁻¹: 3200~2400(br, absorption), 1680, 1630, 1590, 1530, 1470, 1410

NMR(CDCl₃) δ ppm: 1.18(t, J=8 Hz, 3H), 1.6~2.1(m, 3H), 2.3(s, 3H), 2.4~3.1(m, 4H), 7.2(d, J=6 Hz, 2H), 8.6(d, J=6 Hz, 2H), 13.5(br s, 1H)

EXAMPLE 5

4-butylyl-1-methyl-7-(4-pyridyl)5,6,7,8-tetrahydro-3(2H)isoquinolinone

The compound was synthesized in the same procedures as in Example 4 excepting for using propyl bromide instead of ethyl bromide.

mp. 267°~270° C. (decomposition)

NMR(CDCl₃) δ ppm: 0.98(t, J=8 Hz, 3H), 1.74(q, J=8 Hz, 2H), 1.6~2.4(m, 3H), 3.23(s, 3H), 2.4~3.1(m, 6H), 7.2(d, J=6 Hz, 2H), 8.6(d, J=6 Hz, 2H), 13.9(br s, 1H)

EXAMPLE 6

1-methyl-7-(4-pyridyl)5,6,7,8-tetrahydro-4-valeryl-3(2H)isoquinolinone

The compound was synthesized in the same procedures as in Example 4 excepting for using n-butyl bromide instead of ethyl bromide.

mp. 246°~248° C. (decomposition)

NMR(CDCl₃) δ ppm: 0.94(t, J=8 Hz, 3H), 0.8~3.05(m, 13H), 2.30(s, 3H), 7.05(d, J=6 Hz, 2H), 8.46(d, J=6 Hz, 2H), 13.6(br s, 1H)

EXAMPLE 7

4-benzoyl-1-methyl-7-(4-pyridyl)5,6,7,8-tetrahydro-3(2H)isoquinolinone

The compound was synthesized in the same procedures as in Example 4 excepting for using phenyl bromide instead of ethyl bromide.

mp 160°~163° C.

IR $\nu_{max}^{KBr}$cm⁻¹: 1620, 1590, 1550, 1440, 1250, 1200

NMR(CDCl₃) δ ppm: 1.8~2.2(m), 2.16(s, 3H), 2.4~3.2(m), 7.18(d, J=6 Hz, 2H), 7.5(m, 3H), 7.92(m, 2H), 8.56(d, J=6 Hz, 2H), 13.4(br s, 1H) EXAMPLE 8

4-ethyl-1-methyl-7-(4-pyridyl)-5,6,7,8-tetrahydro-3(2H)isoquinolinone

After dissolving 4-acetyl-1-methyl-7-(4-pyridyl)-5,6,7,8-tetrahydro-3(2H)isoquinolinone (4 g), potassium hydroxide (2.3 g) and hydrazine monohydrate (1.4 ml) to ethylene glycol (28 ml), they were heated in a silicon bath and the low boiling fractions were distilled off till the inside temperature reached 190° C.

Subsequently, heating was continued at that temperature for 4 hours and, after cooling, the reaction solution was poured into water (250 ml) and adjusted to pH with 6N-hydrochloric acid. Then, after extraction with chloroform (200 ml), they were dried, concentrated and finally recrystallized from ethanol to obtain 4-ethyl-1-methyl-7-(4-pyridyl)-5,6,7,8-tetrahydro-3(2H)isoquinolinone (1.2 g).

mp. higher than 300° C.

IR $\nu_{max}^{KBr}$cm⁻¹: 3200~2400(br absorption), 1620, 1590, 1530, 1440

NMR(CF₃COOH) δ ppm: 1.26(t, 3H), 2.6(s, 3H), 2.0~3.6(9H, m), 8.1(d, J=6 Hz, 2H), 8.8(d, J=6 Hz, 2H)

| Elementary analysis C₁₇H₂₀N₂O | | | |
|---|---|---|---|
| | C | H | N |
| Calcd. value (%) | 76.09 | 7.51 | 10.44 |
| Measured value (%) | 75.88 | 7.34 | 10.48 |

EXAMPLE 9

1-methyl-4-propyl-7-(4-pyridyl)-5,6,7,8-tetrahydro-3(2H)isoquinolinone 1-methyl-4-propyl-7-(4-pyridyl)-5,6,7,8-tetrahydro-3(2H)isoquinolinone was synthesized from 1-methyl-4-propionyl-7-(4-pyridyl)-5,6,7,8-tetrahydro-3(2H)isoquinolinone synthesized in Example 4 in the same procedures as in Example 7.

mp. higher than 300° C.

NMR(CF₃COOH) δ ppm: 1.10(t, 3H), 2.55(s, 3H), 2.0~3.7(m, 11H), 8.1(d, J=6 Hz, 2H), 8.80(d, J=6 Hz, 2H)

EXAMPLE 10

4-formyl-1-methyl-7-(4-pyridyl)-5,6,7,8-tetrahydro-3(2H)isoquinolinone 1-methyl-7-(4-pyridyl)5,6,7,8-tetrahydro-3(2H)isoquinolinone (2.4 g) was suspended into a mixed solvent of ethanol (15 ml) and water (15 ml) and, after adding potassium hydroxide (4.2 g), heated to 80° C. and chloroform (1.2 ml) was dropped.

Further, potassium hydroxide (2.4 g) and chloroform (1.2 ml) were added for twice alternately over 6 hours.

After cooling to room temperature, they were diluted with water (100 ml), adjusted once to pH 5 with 6N-hydrochloric acid, rendered to an alkaline range again with sodium hydrogen carbonate and then extracted with chloroform (80 ml×3).

The extract was washed with saturated saline water, dried over magnesium sulfate, concentrated and then purified on silica gel column chromatography to obtain 4-formyl-1-methyl-7-(4-pyridyl)-5,6,7,8-tetrahydro-3(2H)isoquinolinone (0.25 g).

mp. 275°~278° C. (decomposition)

NMR(CDCl$_3$) δ ppm: 1.6~3.2(m, 7H), 2.38(s, 3H), 7.2(m, 2H), 8.6(m, 2H), 10.5(br s, 1H), 13.5(br s, 1H)

IR $\nu_{max}^{KBr}$cm$^{-1}$: 3200~2400(br absorption), 1700, 1640, 1600

EXAMPLE 11

1,4-dimethyl-7-(4-pyridyl)-5,6,7,8-tetrahydro-3(2H)isoquinolinone 4-formyl-1-methyl-7-(4-pyridyl)-5,6,7,8-tetrahydro-3(2H)isoquinolinone (0.24 g) obtained in Example 10 was dissolved in methanol (15 ml) and hydrazine monohydrate (0.5 ml) was added and heated under reflux for 2 hours.

After concentration, ethylene glycol (4 ml) and potassium hydroxide (0.22 g) were added to the residue and heated at 200° C. for 3 hours.

After cooling, they were neutralized with 1N-hydrochloric acid, diluted with water (20 ml) and then extracted with chloroform (30 ml×3).

The extract was washed with water, dried, concentrated and then finally recrystallized from methanol to obtain to obtain 1,4-dimethyl-7-(4-pyridyl)-5,6,7,8-tetrahydro-3(2H)isoquinolinone (0.16 g).

mp. higher than 300° C.

NMR(CF$_3$COOD) δ ppm: 2.0~3.6(m, 7H), 2.34(s, 3H), 2.56-(s, 3H), 8.06(d, J=6 Hz, 2H), 8.74(d, J=6 Hz, 2H)

IR $\nu_{max}^{KBr}$cm$^{-1}$: 3200~2400(br absorption), 1640, 1600, 1540, 1470

EXAMPLE 12

4-(1-hydroxyethyl)-1-methyl-7-(4-pyridyl)-5,6,7,8-tetrahydro-3(2H)isoquinolinone 4-acetyl-1-methyl-7-(4-pyridyl)-5,6,7,8-tetrahydro-3(2H)isoquinolinone (20 g) was dissolved into an aqueous ½N-solution of sodium hydroxide and, after adding sodium borohydride (7.96 g), heated under reflux for 4 hours. After cooling, pH was adjusted to 10 with concentrated hydrochloric acid and precipitated crystals were collected by filtration and washed with water and methanol.

The crystals were recrystallized from methanol to obtain 4-(1-hydroxyethyl)-1-methyl-7-(4-pyridyl)-5,6,7,8-tetrahydro-3(2H)isoquinolinone.

mp. 303° C. (decomposition)

IR $\nu_{max}^{KBr}$cm$^{-1}$: 3200, 3000~2400 (br absorption), 1630, 1600, 1540, 1460

NMR(CDCl$_3$) δ ppm: 1.56(d, J=8 Hz, 3H), 1.7~2.4(m, 3H), 2.4~3.2(m, 4H), 2.32(s, 3H), 4.94(m, 1H), 7.22(d, J=6 Hz, 2H), 8.58(d, J=6 Hz), 13.46(br s, 1H)

EXAMPLE 13

4-(hydroxymethyl)-1-methyl-7-(4-pyridyl)-5,6,7,8-tetrahydro-3(2H)isoquinolinone 4-(formyl)-1-methyl-7-(4-pyridyl)-5,6,7,8-tetrahydro-3(2H)isoquinolinone (0.7 g) was dissolved into methanol (40 ml) and sodium borohydride (0.4 g) was added at room temperature.

After stirring at room temperature for 30 minutes, water (10 ml) was added and methanol was distillated under a reduced pressure. After adjusting pH to 5 with 1N-hydrochloric acid, it was again adjusted to an alkaline range with sodium hydrogen carbonate and then extracted with chloroform (30 ml×3).

The extract was washed with water, dried, concentrated and then recrystallized from methanol to obtain 4-(hydrocymethyl)-1-methyl-7-(4-pyridyl)-5,6,7,8-tetrahydro-3(2H)isoquinolinone (0.45 g).

mp. 254°~257° C. (decomposition)

IR $\nu_{max}^{KBr}$cm$^{-1}$: 3200~2400 (br absorption), 1630, 1600, 1540, 1460

NMR(DMSO-D$_6$, CF$_3$COOH) 1.9~3.3(m, 7H), 2.3(s, 3H), 4.5(s, 2H), 8.06(d, J=6 Hz, 2H), 8.9(d, J=6 Hz, 2H)

EXAMPLE 14

4-(2-(2-hydroxypropyl))-1-methyl-7-(4-pyridy)-5,6,7,8-tetrahydro-3(2H)isoquinolinone 4-acetyl-1-methyl-7-(4-pyridyl)-5,6,7,8-tetrahydro-3(2H)isoquinolinone (5.6 g) was added under a nitrogen gas stream to 20% solution of methyl magnesium bromide/tetrahydrofuran and heated under reflux for 2.5 hours.

After cooling, the reaction solution was poured into water (200 ml) and after adjusting to pH 4 with 6N-hydrochloric acid, again rendered to an alkaline range with sodium hydrogen carbonate and extracted with chloroform (100 ml×3).

The extract was washed with water, dried, concentrated and finally recrystallized from methanol to obtain 4-(2-(2-hydroxypropyl))-2-methyl-7-(4-pyridyl)-5,6,7,8-tetrahydro-3(2H)isoquinolinone (5.2 g).

mp. higher than 300° C.

IR $\nu_{max}^{KBr}$cm$^{-1}$: 3200~2400 (br absorption), 1620, 1420

NMR(CDCl$_3$) δ ppm: 1.6(s, 3H), 1.7(s, 3H), 1.6~2.5(m, 3H), 2.2(m, 3H), 2.5~3.2(m, 4H), 7.16(d, J=6 Hz, 2H), 8.5(d, J=6 Hz, 2H), 8.6(s, 1H), 13.5(br s, 1H)

EXAMPLE 15

4-isopropenyl-1-methyl-7-(4-pyridyl)-5,6,7,8-tetrahydro-3(2H)isoquinolinone 4-(2-(2-hydroxypropyl))-1-methyl-7-(4-pyridyl)-5,6,7,8-tetrahydro-3(2H)isoquinolinone (0.9 g) obtained in Example 14 was dissolved into dichloromethane (15 ml) and diethylesilane (0.6 ml) and trifluoroacetic acid (2.4 ml) was added and stirred at room temperature for 17 hours.

The solution was poured into a saturated aqueous solution of sodium hydrogen carbonate and extracted with chloroform (80 ml×3).

The extract was washed with water, dried, concentrated and finally recrystallized from chloroform/ethanol to obtain 4-isopropenyl-1-methyl-7-(4-pyridyl)-5,6,7,8-tetrahydro-3(2H)isoquinolinone (0.6 g).

mp. higher than 300° C.

IR $\nu_{max}^{KBr}$cm$^{-1}$: 3200~2400 (br absorption), 1630, 1600, 1530, 1470

NMR(CDCl$_3$) δ ppm: 1.6~2.6(m, 3H), 2.05(s, 3H), 2.26(s, 3H), 2.6~3.1(m, 4H), 4.9(m, 1H), 5.3(m, 1H), 7.2(d, J=6 Hz, 2H), 8.56(d, J=6 Hz, 2H), 13.4(br s, 1H)

EXAMPLE 16

1-methyl-4-pentafluoroethyl-7-(4-pyridyl)-5,6,7,8-tetrahydro-3(2H)isoquinolinone 1-methyl-7-(4-pyridyl)-5,6,7,8-tetrahydro-3(2H)isoquinolinone (0.24 g) was suspended in dimethylformamide (5 ml) and 60% sodium hydride (oily) (0.06 g) was added.

After heating to 50° C. into a uniform solution, it was cooled and perfluoroethylphenyl iodonium trifluoromethane sulfonate (0.47 g) was added and stirred at room temperature for 2 days.

After diluting the reaction solution with water (20 ml), it was rendered acidic (pH 2) with 1N-hydrochloric acid and again alkaline with sodium hydrogen carbonate and, after adding water (50 ml) further, it was extracted with chloroform (50 ml×3).

The extract was dried, concentrated and purified on silica gel column chromatography to obtain 1-methyl-4-pentafluoroethyl-7-(4-pyridyl)-5,6,7,8-tetrahydro-3(2H)isoquinolinone (0.11 g).

mp. 265°~300° C. gradual decomposition

IR $\nu_{max}^{KBr}$ cm$^{-1}$: 3200~2400 (br absorption), 1640, 1600

NMR(CDCl$_3$) δ ppm: 1.6~2.4(m, 3H), 2.3(s, 3H), 2.5~3.3(m, 4H), 7.2(d, J=6 Hz, 2H), 8.6(d, J=6 Hz, 2H), 13.7(br s, 1H), Mass: M/Z=358(M$^+$)

EXAMPLE 17

4-ethyl-1-methyl-7-(2-pyridyl)-5,6,7,8-tetrahydro-3(2H)isoquinolinone 4-ethyl-1-methyl-7-(2-pyridyl)5,6,7,8-tetrahydro-3(2H)isoquinolinone was synthesized from 4-acetyl-1-methyl-7-(2-pyridyl)-5,6,7,8-tetrahydro-3(2H)isoquinolinone in the same procedures as in Example 8.

mp. 300° C.

NMR(CDCl$_3$) δ ppm: 1.1(t, J=6 Hz, 3H), 1.8~2.4(m, 3H), 2.3(s, 3H), 2.4~3.3(m, 6H), 7.0~7.4(m, 2H), 7.6(m, 1H), 8.55(m, 1H)

Example 18

4-(2-(2-hydroxypropyl))-1-methyl-7-(2-pyridyl)-5,6,7,8-teterahydro-3(2H)isoquinolinone 4-(2-(2-hydroxypropyl)-1-methyl-7-(2-pyridyl)-5,6,7,8-tetrahydro-3(2H)isoquinolinone was synthesized from 4-acetyl-1-methyl-7-(2-pyridyl)-5,6,7,8-tetrahydro-3(2H)isoquinolinone in the same procedures as in Example 14.

mp. 300° C.

IR $\nu_{max}^{KBr}$ cm$^{-1}$: 3100~2400 (br absorption), 1630, 1440

NMR(CDCl$_3$) δ ppm: 1.6(s, 3H), 1.7(s, 3H), 2.3(s, 3H), 1.6~2.3(m, 3H), 2.6~3.2(m, 4H), 7.0~7.3(m, 2H), 7.6(m, 1H), 8.5(m, 1H), 8.75(br s, 1H)

EXAMPLE 19

4-isopropenyl-1-methyl-7-(2-pyridyl)-5,6,7,8-teterahydro-3(2H)isoquinolinone 4-isopropenyl-1-methyl-7-(2-pyridyl)-5,6,7,8-tetrahydro-3(2H)isoquinolinone was synthesized from 4-(2-(2-hydroxypropyl))-1-methyl-7-(2-pyridyl)-5,6,7,8-tetrahydro-3(2H)isoquinolinone obtained in Example 18.

mp. higher than 300° C.

NMR(CDCl$_3$) δ ppm: 2.0(s, 3H), 2.25(s, 3H), 1.8~2.4(m, 3H), 2.6~3.2(m, 4H), 4.8(m, 1H), 5.25(m, 1H), 7.0~7.3(m, 2H), 7.6(m, 1H), 8.5(m, 1H)

IR $\nu_{max}^{KBr}$ cm$^{-1}$: 3200~2400 (br absorption), 1640, 1595, 1540, 1480

TEST EXAMPLE 1

Pharmacological Test

Mongrel dogs of either sex, weighing 8 to 12 kg, were anesthetized with sodium pentobarbital (30 mg/kg i.v.). The left ventricular pressure (LVP) was measured with a sensor tip transducer and the maximum rate of rise of LVP (LV dP/dtmax) was calculated by an electronic differentiator. Polyethylene cannulae were inserted into the femoral artery to measure systemic blood pressure (BP) and into the femoral veins for administration or infusion of chemicals. BP was measured with a pressure transducer and heart rate (HR) by a cardiotachometer from the pressure pulse. The respective parameters were simultaneously recorded on a multichannel polygraph.

To induce and maintain heart failure state, propranolol was administered in a bolus injection (4 mg/kg i.v.) followed by an infusion (0.1 mg/kg/min i.v.). After the state was stable, i.e., BP, HR and LVP were slightly and LV dP/dtmax was markedly decreased, the tested chemicals were administered. The dose of tested chemicals required for recovering the reduction in the LV dP/dtmax to the value before the propranolol administration was determined and defined as an ED100. The changes in BP and HR at ED100 were expressed by the variation coefficient relative to the values of the stable state. The results are shown in the Table below.

| Compound Example | ED$_{100}$ (mg/Kg, iv) | Blood pressure (%) | Number of heart beat % |
|---|---|---|---|
| 1 | 1.0 | −32.1 | +17.3 |
| 2 | 3.0 | −11.5 | +18.3 |
| 3 | 3.0 | −27.8 | +30.6 |
| 4 | 3.0 | −18.0 | +26.2 |
| 5 | 3.0 | −20.2 | +23.7 |
| 6 | 3.0 | −10.5 | +19.8 |
| 7 | 3.0 | −28.3 | +29.6 |
| 8 | 0.03 | −22.5 | +25.3 |
| 9 | 0.3 | −16.6 | +14.4 |
| 10 | 3.0 | −17.5 | +24.2 |
| 11 | 0.3 | −28.5 | +21.0 |
| 12 | 3.0 | −19.7 | +22.5 |
| 13 | 0.3 | −2.6 | +20.0 |
| 14 | 0.1 | −9.3 | +32.6 |
| 15 | 0.03 | −16.4 | +28.6 |
| 16 | 3.0 | −15.9 | +29.1 |
| 17 | 0.1 | −2.1 | +15.0 |
| 18 | 0.3 | −8.3 | +30.1 |
| 19 | 0.1 | −15.9 | +27.6 |

TEST EXAMPLE 2

Acute toxicology

Single-dose LD50 values were determined in male mice (ddy, 5w) following oral administration. The tested chemicals were dissolved or suspended in physiological saline. As a result, the LD50 values of the tested chemcials were greater than 600 mg/kg.

What is claimed is:

1. An Isoquinoline derivative represented by the general formula (I):

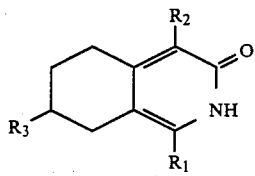

where
- $R_1$ represents a lower $C_1$–$C_4$ alkyl group or cyclopropyl group,
- $R_2$ represents formyl group, benzoyl group, lower $C_1$–$C_4$ alkyl group, lower $C_1$–$C_4$ alkenyl group, lower $C_1$–$C_4$ hydroxy substituted alkyl group and $C_1$–$C_4$ perfluoroalkyl group and
- $R_3$ represents 4-pyridyl group or 2-pyridyl group respectively, or a therapeutically acceptable salt thereof.

2. A compound as defined in claim 1, which is 4-ethyl-1-methyl-7-(4-pyridyl)-5,6,7,8-tetrahydro-3(2H)isoquinolinone.

3. A compound as defined in claim 1, which is 4-ethyl-1-methyl-7-(2-pyridyl)-5,6,7,8-tetrahydro-3(2H)isoquinolinone.

4. A compound as defined in claim 1, which is 4-isopropenyl-1-methyl-7-(4-pyridyl)-5,6,7,8-tetrahydro-3-(2H)isoquinolinone.

5. A compound as defined in claim 1, which is 4-isopropenyl-1-methyl-7-(2-pyridyl)-5,6,7,8-tetrahydro-3(2H)isoquinolinone.

* * * * *